(12) United States Patent
Foster

(10) Patent No.: US 6,874,927 B2
(45) Date of Patent: Apr. 5, 2005

(54) ORTHOPAEDIC CEMENT MIXING AND DISPENSING DEVICE

(75) Inventor: David R. Foster, Woodstock (GB)

(73) Assignee: Summit Medical Limited, Gloucestershire (GB)

( * ) Notice: Subject to any disclaimer, the term of this patent is extended or adjusted under 35 U.S.C. 154(b) by 64 days.

(21) Appl. No.: 10/182,659

(22) PCT Filed: Jan. 31, 2001

(86) PCT No.: PCT/EP01/01005
§ 371 (c)(1),
(2), (4) Date: Dec. 9, 2002

(87) PCT Pub. No.: WO01/56514
PCT Pub. Date: Aug. 9, 2001

(65) Prior Publication Data
US 2003/0103408 A1 Jun. 5, 2003

(30) Foreign Application Priority Data
Jan. 31, 2000 (GB) .............................. 0002190

(51) Int. Cl.⁷ .............................................. B01F 13/06
(52) U.S. Cl. ...................... 366/139; 366/244; 366/288
(58) Field of Search ........................ 366/139, 242–247, 366/252, 288

(56) References Cited

U.S. PATENT DOCUMENTS

| | | | |
|---|---|---|---|
| 4,577,973 A | * 3/1986 | Occelli ........................ 366/139 |
| 5,265,956 A | * 11/1993 | Nelson et al. ............... 366/139 |
| 5,344,232 A | * 9/1994 | Nelson et al. ............... 366/139 |
| 5,368,386 A | * 11/1994 | Murray ........................ 366/139 |
| 5,395,167 A | 3/1995 | Murray |
| 5,415,474 A | * 5/1995 | Nelson et al. ............... 366/139 |
| 5,549,381 A | 8/1996 | Hays et al. |
| 5,558,136 A | 9/1996 | Orrico |
| 5,797,678 A | * 8/1998 | Murray ........................ 366/139 |
| 5,797,679 A | * 8/1998 | Grulke et al. ............... 366/139 |
| 5,876,116 A | 3/1999 | Barker et al. |
| 6,024,480 A | * 2/2000 | Seaton et al. ............... 366/130 |
| 6,536,937 B1 | * 3/2003 | Burchett ...................... 366/139 |

FOREIGN PATENT DOCUMENTS

| | | |
|---|---|---|
| EP | 0 768 067 A2 | 4/1997 |
| EP | 0 768 067 A3 | 2/1998 |
| WO | WO 93/10892 | 6/1993 |
| WO | WO 93/22041 | 11/1993 |
| WO | 95/00240 | * 1/1995 |
| WO | 99/67015 | * 12/1999 |

* cited by examiner

Primary Examiner—Charles E. Cooley
(74) Attorney, Agent, or Firm—Alix, Yale & Ristas, LLP

(57) ABSTRACT

The apparatus is a mixing and dispensing device for orthopaedic bone cement, comprising an introducer funnel and a mixing syringe body. A mixing shaft and paddle arrangement extends through the funnel and mixing chamber, the paddle having a profile matching the shape of the funnel, in the introducer funnel.

6 Claims, 3 Drawing Sheets

ORTHOPAEDIC CEMENT MIXING AND DISPENSING DEVICE

BACKGROUND OF THE INVENTION

The present invention relates to a device for mixing and delivering orthopaedic bone cement or the like.

Orthopaedic bone cement is used throughout the world to secure hip, knee and other anatomic prostheses in an appropriate anatomical position. The bone cement is produced by thoroughly mixing together two components, usually methylmethacrylate monomer liquid and polymethylmethacrylate powder. The mixing was previously carried out using a simple bowl and spatula. The surgeon then removes the required amount of cement and manipulates it by hand before inserting it into a preformed cavity or applying it to a resected bony surface where the prosthesis is to be positioned. Cement may either be applied by hand or may be put into a syringe and applied thereby.

Several improvements have been made to this mixing arrangement, including providing arrangements for mixing under vacuum, and to improve the mixing efficiency, to result in a homogenous cement material.

Several devices for mixing cement, usually in a vacuum, are presently available and in general use.

Of the available devices, the preferred forms are the 'bowl' type mixers and the 'syringe' mixers.

Bowl type mixers are provided usually in the form of hand-held mixing bowls. The substances to be mixed are placed in the bowl to which a vacuum is applied. The substances are mixed by means of a rotating paddle extending into the bowl, which is rotated manually by means of a handle extending through the lid of the bowl. In some applications, the use of such a mixing bowl, an example of which is disclosed in EP-A-0616552, is favoured. Many surgeons prefer to 'hand pack' the cement. Bowl mixing also tends to be preferred by nurses who are used to the convenience of mixing in this vessel. A bowl is easier to use and it is important that the nurses feel confident, since timing is very crucial and the mixture must be 'right first time'. Many surgeons also tend to prefer bowl mixers. It is crucial that the mixture does not begin to set before it is applied and experienced surgeons can tell, by touch, when the cement is at the right stage for applying to the bone cavity.

These 'bowl' mixers are in widespread use and are very popular. They are easy to use, allowing repeatable consistent mixing, independent of the level of skill of the user, and the concept of mixing used by the bowl is simple and is popular with nurses. The bowl type mixer is very flexible in that it can be used to mix all types of cement and can be used to mix varying quantities of cement. In bowl mixers where a high vacuum is applied, the cement has low porosity and thus high strength.

In the bowl mixer of EP-A-0616552, which has a 'rotating axis', as opposed to the paddle having a fixed axis, the cement is very thoroughly mixed and the chances of 'dead spots' or areas of unmixed cement occurring are very small.

In some applications, it is preferable or even necessary, to apply the mixed cement to the bone or bone cavity by means of a syringe. Indeed, many surgeons prefer syringe-type application to 'hand packing'.

If, for such applications, the cement is initially mixed in a bowl as described above, it must then be transferred to a dispensing syringe. This transfer can be messy and time-consuming and may expose the mixture to more air entrapment. The introduction of air into the cement produces a weak cement, which has obvious disadvantages.

To overcome this problem, mixing devices have been designed which combine a mixing chamber and a syringe. For example, EP-A-0178658 discloses a device for mixing bone cement comprising a mixing container connected to a feed device. A vacuum source is connected to the feed device for mixing the substances under vacuum. This device has proved to be a very efficient mixing and transfer system and eliminates the need to transfer the mixed cement from the mixing bowl to a syringe.

U.S. Pat. No. 4,758,096 and U.S. Pat. No. 3,606,094 also disclose bone cement mixers in which the cement is mixed in the dispensing vessel itself. In the first of these patents, the mixing is effected manually by means of a 'masher' plate-type agitator. The masher plate is attached to a shaft attached to a handle. The agitator is moveable in the chamber both axially and rotatably to permit mixing of the cement by the user, moving the handle vertically and rotatably. However, such mixing operation is difficult and inefficient and does not guarantee thorough mixing of the cement. Partial strokes of the 'masher' can lead to areas of unmixed powder and the mixing is not consistent, and is reliant on the consistency of the user.

Another problem with the 'masher' type system is that it is difficult to mix standard viscosity cement using this plunger. As the plate is pushed down into the cement, it meets a high resistance, which can result in only a partial mixing stroke being carried out and the cement being compacted at the base of the mixing chamber.

Other, improved mix-in-the-syringe mixers are disclosed in, for example, DE-C-883326 and EP-A-0744991.

Again, these mix-in-the-syringe mixers have become very popular and are in widespread use.

The mix-in-the-syringe mixers are very useful where relatively small quantities of cement are mixed and used. Most mixers on the market are designed to be able to mix up to a 'double' mix of the highest volume cement currently in common use (e. g. Simplex Cement).

Several different types of cement are commonly used in orthopaedic applications. These cements have very different characteristics and volumes, and also have different viscosities. Table 1 below shows three of the most commonly used cement types, showing approximate volumes of dry powder, and the corresponding volume of mixed cement.

Cement Volumes:

| Cement Type | Dry Powder Volume mm$^2$ | Mixed Cement Volume mm$^2$ |
| --- | --- | --- |
| SIMPLEX (USA) | 302,000 | 135,000 |
| PALACOS | 125,000 | 130,000 |
| CMW | 130,000 | 139,000 |

From the above table, it can be seen that cements such as SIMPLEX have a dry powder volume roughly three times that of other cements, to produce the same volume of mixed cement.

Thus, generally, for mix-in-the-syringe mixers, the mixing chamber must be large enough to receive, say, a double mix of dry powder of the highest volume cement commonly used, even though the actual volume of mixed cement is considerably less. This means that generally the body of the syringe or the mixing chamber is, in fact, much larger than necessary for other types of cement, and requires a longer mixing stroke than would be required for the other low volume cements.

In some cases, the surgeon will wish to prepare an even larger quantity of cement, e. g. a triple mix. Larger amounts of cement are required, for example, in a revision operation, or for certain types of primary hips.

Such larger quantities can generally be mixed in a bowl-type mixer, as described, for example, in EP-A-0616552. However, with the syringe-type mixers, it is generally not possible to merely increase the dimensions of the mixing chamber, to allow more cement to be mixed.

Increasing the height of the mixing chamber to accommodate the larger quantity of cement is not feasible, as this results in a device which is just too big to handle comfortably. The longer the chamber is, the more difficult it becomes to introduce the mixing paddle through the column in a correct alignment and to locate the paddle correctly. This is particularly so when the cement becomes more dense and it becomes extremely difficult to push the paddle down and to cause effective mixing.

Thus, there is a need for an effective and efficient, easy to handle, mix-in-the-syringe type orthopaedic cement mixer which is not unnecessarily big or which is capable of mixing large, e. g. triple, mixes of cement, even when the cement used is a large volume cement, such an simplex.

One mixer which aims to deal with this problem is produced by Stryker, and is described in U.S. Pat. No. 5,558,136 and associated patents. This mixer comprises a funnel section, leading into a cylindrical syringe body mixing chamber. A mixing paddle extends through the funnel section and is rotated by means of a handle in the lid of the funnel section. A large quantity of powder can then be inserted into the device through the funnel. When the monomer is added, and the cement powder and monomer mix, the resulting mixture has a smaller volume which is accommodated within the syringe body. The funnel part may then be removed, leaving a simple syringe body for attachment to a syringe gun and nozzle. However, this device relies on the use of low viscosity cement which, as mixed, falls, under gravity, into the syringe body mixing chamber. It is also essential that the mixing phase is started straight away, as soon as the monomer is added, before the mixture starts to 'dough up'.

A problem is that unmixed powder can be left in the funnel as the cement reduces, which does not fall into the syringe body mixing chamber.

This can result in the unmixed powder falling into the mixed cement as the funnel part is removed, resulting in dry or dead spots and, thus, a brittle cement.

Another problem is that when mixing standard cements or where mixing is not started straight away, the doughing-up cement can stick to the walls of the funnel and the paddle causing high wastage.

SUMMARY OF THE INVENTION

The present invention aims to overcome the problems associated with this device and, according to one aspect, provides an apparatus for mixing orthopaedic cement, comprising a first funnel or bowl shaped introduction chamber, removably attached to one end of a second cylindrical mixing chamber, adapted to form the body of a dispensing syringe; and a mixing mechanism comprising a rotatable shaft extending through the first and second chambers, the shaft having at least one radially extending blade, characterised in that the profile of the at least one blade in the first chamber tapers inwards, towards the second chamber, and extends into and substantially along the length of the second chamber.

It is preferable that the shaft is arranged to rotate about its own axis and also that its axis of rotation itself rotates around the chambers. The use of a rotational axis mixing mechanism enables cement to be more thoroughly mixed. The blades are better able to cut through cement even when it is fairly solid.

According to a second aspect, there is provided an apparatus for mixing orthopaedic cement, comprising a first funnel or bowl shaped introduction chamber, removably attached to one end of a second cylindrical mixing chamber, adapted to form the body of a dispensing syringe; and a mixing mechanism comprising a rotatable shaft extending through the first and second chambers, the shaft having at least one radially extending blade, characterised in that the shaft is rotated by rotation means connected to the shaft by a gear mechanism; wherein rotation of said rotation means causes said shaft to rotate about its own axis and also moves the axis of rotation of said shaft within said chambers.

The funnel chamber preferably also has a lid which preferably carries a rotatable handle, which is connected, e. g. by a gear mechanism, to the shaft, to rotate the shaft. The shaft may be rotated by other means, e. g. a pneumatic drill.

Preferably, means are provided to apply a vacuum to the insertion and mixing chambers, for mixing the cement under vacuum.

BRIEF DESCRIPTION OF THE DRAWINGS

Preferred embodiments of the invention will now be described, by way of example only, with reference to the accompanying drawings.

DETAILED DESCRIPTION OF THE PREFERRED EMBODIMENTS

Figure 1:
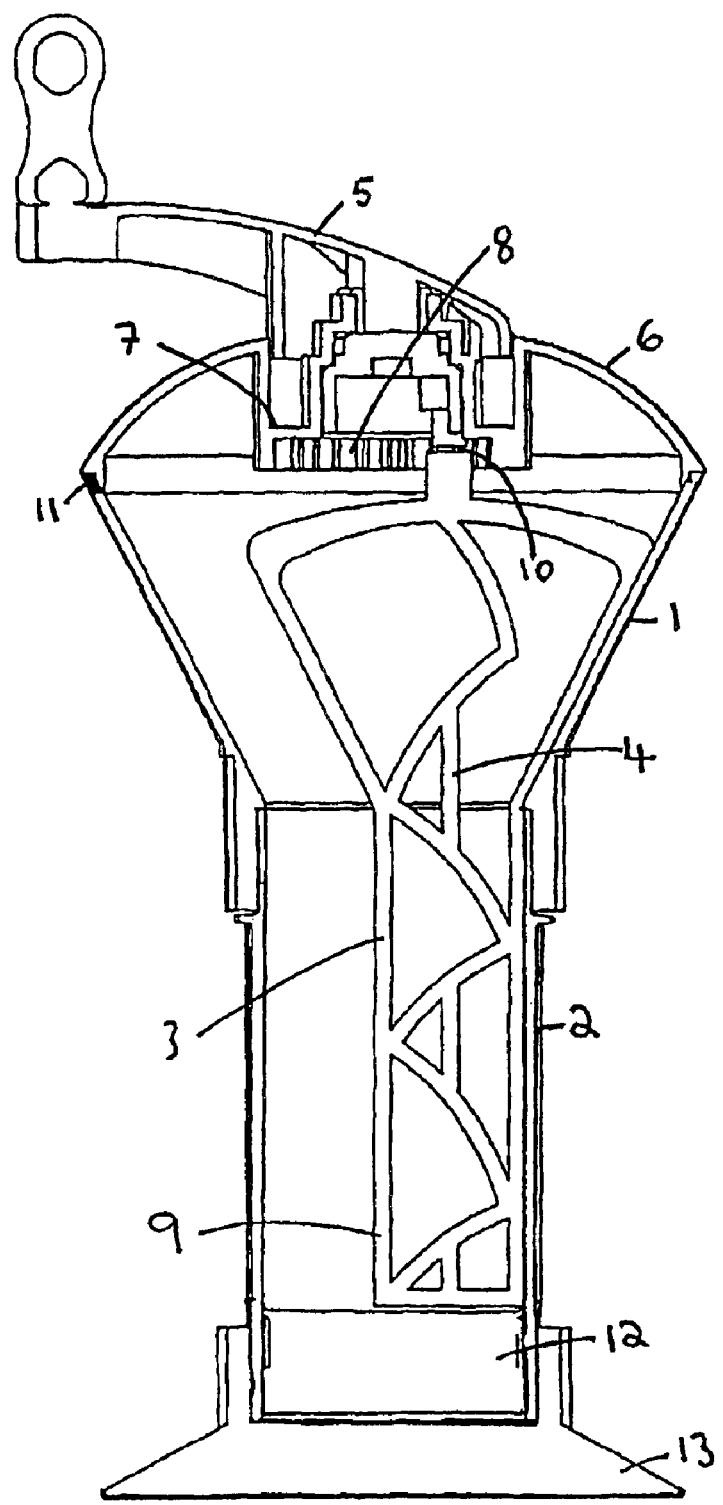
FIG. 1 shows a cross-section through a mixer in accordance with the invention, assembled and ready for mixing.

The mixing apparatus comprises a first funnel chamber 1 and a second, cylindrical mixing chamber 2. A mixing paddle 3 extends through both chambers comprising at least one blade supported by a rotatable shaft 4. The shaft, and, therefore, the mixing paddle, is rotated by means of a handle 5. The handle is mounted in a lid 6 adapted to be sealingly fitted onto the top of the funnel 1. A gear mechanism 7 is provided to cause rotation of the shaft 4 about its own axis, as well as rotation of the shaft axis around the mixing chambers.

The preferred gear mechanism comprises a fixed, circular, toothed rack 8 arranged coaxially with respect to the rotation axis of the handle 5, and provided on the underside of the lid 6. The mixing paddle 3 comprises radially extending mixing blades 9, mounted on the shaft 4. The shaft 4 is rotatably mounted, at one end, into the handle 5. A cog-wheel 10 is fixedly attached to the upper part of the shaft 4 for intermeshing engagement with the toothed rack 8.

The lid is preferably also provided with a vacuum port 14 for connection to a vacuum pump (not shown). The lid 6 is preferably provided with a seal 11 for sealing between the lid and the rim of the funnel 1. Locking means 15 may also be provided between the lid 6 and the funnel 4 and these means will be discussed further below.

The funnel 1 is fitted over one end of the mixing cylinder 2 in a sealing engagement. The connection may be by means of a pushfit or a screw thread, for example.

A plunger 12 for ejecting the mixed cement is slidingly located in the other end of the cylinder 2. This same end of the cylinder 2 is adapted to be received in a stand 13 and may be secured to the stand by corresponding screw threads. A seal may also be provided between the cylinder body 1 and the stand 13.

The method of use of the mixing apparatus will now be described.

Figure 2:
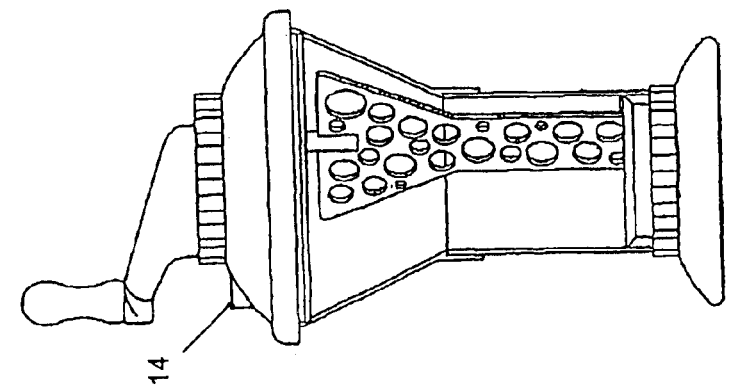
FIG. 2 shows a front perspective view of an assembled mixer.

The mixing apparatus is provided to the user in assembled form, as shown in FIGS. 1 and 2.

Figure 6:
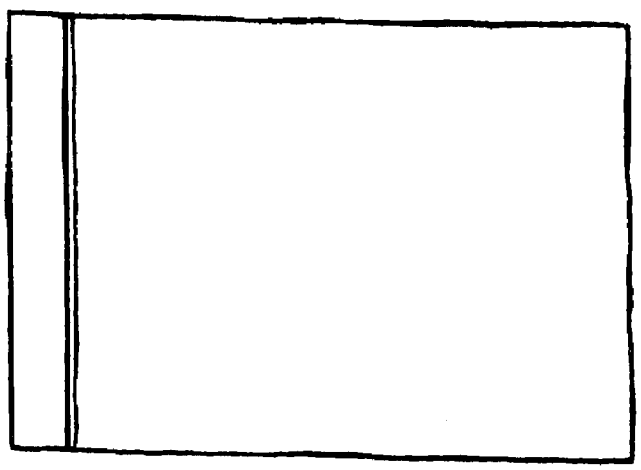
FIG. 6 shows a closed bag containing cement.
Figure 5:
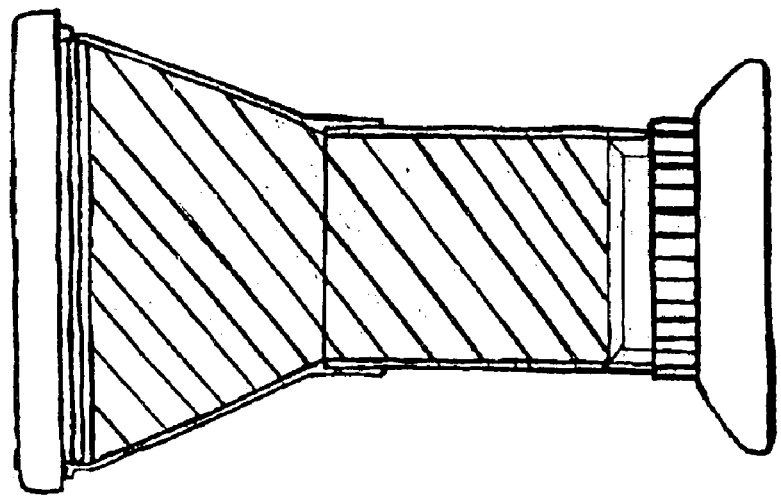
FIG. 5 shows a pre-filled mixer.

In one embodiment, the apparatus is provided as a prefilled device 16, i.e. the cement is already provided in the mixer, e.g. in a closed bag 17 or some other retaining means, as shown in FIGS. 5 and 6.

In the case of the pre-filled container, the closed bag 17 or retaining means is removed, leaving the cement in the chamber.

Figure 3:
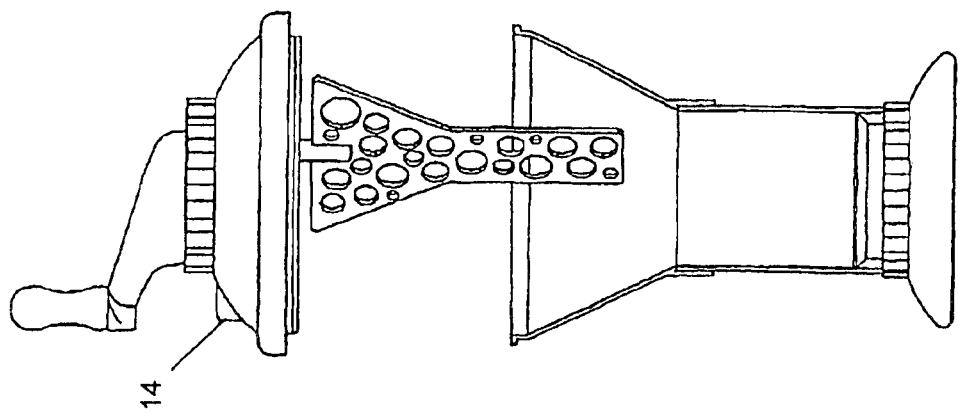
FIG. 3 shows the mixer of FIG. 2 with the lid removed.

Alternatively, where the mixer in not pre-filled, the lid 6 and attached mixing arrangement is removed, as shown in FIG. 3, and the cement powder is inserted into the funnel.

The dry cement powder falls through the funnel 1 and into the cylindrical mixing chamber 2.

For large mixes, or where high volume powder cements are used, the amount at dry powder required will fill the cylindrical chamber 2 and will also extend into the funnel part 1.

The funnel shape allows a greater volume of dry cement powder to be accommodated and the wider top part makes the introduction of cement without spillage, easier.

The monomer ampoule is then broken and added to the cement in the mixing device and the lid is replaced in sealing engagement with the open mouth of the funnel as shown in FIG. 2.

Where the mixing is carried out under vacuum, the vacuum port is connected via a length of PVC tubing (not shown) to the vacuum pump to create a vacuum. Mixing of the cement components is then carried out by rotation of the handle 5 by the user. The complete mixing apparatus may be held in the hand or may be placed in the base 13 and supported on a flat surface such as a table.

The mixing paddle blades 9 have a novel shape resulting in many of the advantages of the present invention.

The paddle extends essentially along the length of the shaft through the funnel chamber 1 and through the mixing chamber 2. The paddle is widest at the top of the funnel chamber, nearest to the lid and then tapers inwards, towards the cylinder chamber 2. The paddle then extends through the chamber with an essentially constant radial dimension.

The profile of the mixing blade 9 in the funnel chamber 1 is such that it will push the cement powder down into the cylindrical chamber, as the components are mixed. As the two components mix, the volume of cement reduces and when completely mixed, the cement will be accommodated within the cylindrical chamber 2.

The paddle in the funnel chamber 1 may also be provided with a feather edge to aid in brushing the unmixed cement powder down into the lower chamber as the mixing cement starts to reduce in volume, the feather edge reduces friction, but enables contact with the funnel.

As a main purpose of the blade profile in the funnel section 1 is to push unmixed cement powder down into the mixture, rather than to actually effect mixing, the profile of the blade in this section can be minimal. This also reduces cement wastage within the blade profile in this section.

Thus, during mixing, all of the cement powder is incorporated into the mix and none is left around the upper edges of the funnel part 1, as in the prior art systems mentioned above.

The more thorough mixing of the cement, required to avoid 'dead spots' of unmixed cement, is carried out in the cylindrical second chamber 2. Here, therefore, the paddle should have a strong, preferably reinforced, profile to ensure that even stiff cement can be very thoroughly mixed.

The end of the mixing paddle furthest from the funnel part 1 may be provided with a feather edge to travel over the piston 12.

It is also preferable that the paddle in this second chamber 2 is relatively flat and thin, with a cutting profile allowing it to cut through thick cement, as it rotates. This reduces the resistance between the mixed cement, as it starts to set, and the mixing paddle, resulting in more thorough mixing.

Although the present invention has particular advantages over the prior art because of its unique design and the design of the paddle, the mixing efficiency of the device is further improved if a 'rotating axis' mechanism is used, rather than a fixed axis rotating paddle.

With the rotating axis arrangement, the operator rotates the handle 5 which causes planetary movement of the shaft 4 about its central axis and, at the same time, causes the cog-wheel 10 to mesh with the rack 8 so as to drive the cog-wheel 10, producing rotation of a paddle 3 about the axis of the shaft 4. Thus, due to the gear mechanism provided by the toothed rack 8 and the cog-wheel 10, rotation of the handle 5 causes the paddle 3 to move around the mixing chambers 1, 2 in planetary fashion and, at the same time, to rotate about its own axis.

Such a mechanism enables the paddle 3 to rotate several times for each turn of the handle 5 and results is in a more than 90% coverage of the mixing chamber area. Preferably, one rotation of the handle 5 does not cause a whole number of rotations of the paddle 3, so the paddle is in a different orientation at the beginning and end of a particular cycle of the axial movement. This helps to avoid dead spots being formed in the cement and improves mixing.

In the cylindrical second chamber 2, at least one blade 9 should extend from the shaft 4 to the wall of the chamber 2. Other blades may only extend partway across the bowl.

FIGS. 1 and 2 show two possible different blade designs, which allow for thorough mixing, whilst minimising the amount of material required to form the blades. Other blade designs may be used, within the scope of the claims.

Once the cement is thoroughly mixed (the surgeon can visually monitor this by viewing through the transparent walls of the container or through a viewing window provided in the container, and an experienced surgeon will also be able to tell by the resistance of the cement to mixing, whether the cement is ready), the funnel chamber 1, the lid 6 and the mixing paddle 3 are removed from the cylindrical mixing chamber 2.

Figure 4:
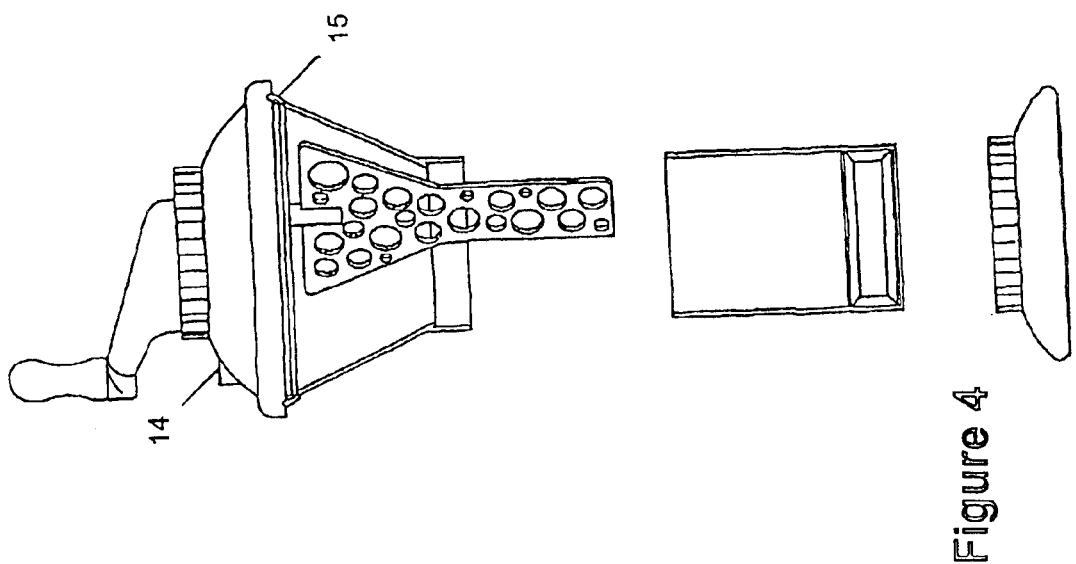
FIG. 4 shows the mixer of FIG. 2 with the lid, funnel and base removed.

Whilst all of these parts can be removed individually, in the preferred embodiment, the lid, to which the mixing mechanism is already attached, is provided with a locking arrangement 15 to lock it to the funnel part 1, so that these parts can all be removed together as shown in FIG. 4. This reduces the risk of any remaining unmixed cement powder in the top part of the funnel chamber 1 falling into the mixed cement. A blade wiping slot may be introduced between the funnel and the syringe, through which the blade is drawn as it is removed, to ensure that all the mixed cement remains in the cylindrical chamber 2.

An applicator nozzle (not shown) is then attached to the open end of the cylindrical chamber 2, from which the funnel chamber 1 has been removed. The cylindrical chamber 2 is also removed from the base 13, if the base has been used. The mixed cement is then forced through the nozzle under the action of the plunger 12, to be applied to the appropriate site. Different types of plunger may be used to force the cement out through the nozzle, for example a hand-operated gun may be used or a gas powered pressure gun. The dispensing mechanism may be as described in, for example, EP-A-0744991.

The fact that the funnel chamber 1 is used in combination with the mixing chamber 2, allows larger quantities of cement to be mixed, and the cylindrical mixing chamber 2, which forms the body of the dispensing syringe, need only be large enough to accommodate the mixed cement volume. This can, when cements such as Simplex are used, be considerably less than the unmixed volume.

The use of a shorter mixing chamber 2 reduces the resistance to the insertion of the paddle. Furthermore, the syringe body will actually be full of mixed cement, when dispensing is begun which reduces the chances of air entrapment. (In other mix-in-the-syringe mixers, the syringe body needs to be large enough to accommodate the unmixed cement and, therefore, when large volume cements are used, after mixing, and prior to dispensing, the syringe body may only be ⅓ full.) The use of a shorter syringe body also reduces the required strokes of the piston to dispense the cement which is less strenuous for surgeons.

Other advantages of a smaller cylindrical body are that a stronger component can be achieved due to the use of a smaller moulding and the risk of failure is reduced. Obviously, there is also a reduced material wastage.

It is envisaged that different syringe sizes can be used in this invention, according to the different volumes and types of cement being used. This provides greater flexibility to the user and optimises the syringe body size. Essentially, using the present invention, the shortest possible syringe body size can be used for the maximum desired quantity of mixed cement. It is envisaged that existing syringe bodies could be used with the present invention.

The present arrangement thus results in a mixing apparatus in which large quantities of cement can be efficiently and thoroughly mixed and dispensed. The system is easy to use, and uses a familiar mixing motion, popular with users.

What is claimed is:

1. An apparatus for mixing orthopaedic cement, comprising a first funnel or bowl shaped introduction chamber removably attached to one end of a second cylindrical mixing chamber, adapted to form the body of a dispensing syringe; and a mixing mechanism comprising a rotatable shaft extending through the first and second chambers, the shaft having at least one radially extending blade, characterized in that the profile of the at least one blade in the first chamber tapers inwards, towards the second chamber, and extends into and substantially along the length of the second chamber, wherein the shaft is arranged to rotate about its own axis and the axis of rotation of the shaft rotates around the chambers.

2. The apparatus as claimed in claim 1, wherein the introduction chamber further comprises a lid which carries a rotatable handle, which is connected to the shaft, to rotate the shaft.

3. The apparatus as claimed in claim 2, wherein locking means are provided to secure said lid to said introduction chamber.

4. The apparatus as claimed in claim 1, wherein means are provided to apply a vacuum to the introduction and mixing chambers, for mixing the cement under vacuum.

5. The apparatus as claimed in claim 1, wherein said mixing chamber is pre-filled with orthopaedic cement.

6. An apparatus for mixing orthopaedic cement, comprising a first funnel or bowl shaped introduction chamber removably attached to one end of a second cylindrical mixing chamber, adapted to form the body of a dispensing syringe; and a mixing mechanism comprising a rotatable shaft extending through the first and second chambers, the shaft having at least one radially extending blade, characterized in that the profile of the at least one blade in the first chamber tapers inwards, towards the second chamber, and extends into and substantially along the length of the second chamber, wherein said mixing chamber is pre-filled with orthopaedic cement provided in a sealed bag contained within said mixing chamber.

* * * * *